(12) United States Patent  
Seward

(10) Patent No.: US 7,070,606 B2  
(45) Date of Patent: Jul. 4, 2006

(54) METHODS AND APPARATUS FOR ASPIRATION AND PRIMING OF INFLATABLE STRUCTURES IN CATHETERS

(75) Inventor: Kirk Patrick Seward, Dublin, CA (US)

(73) Assignee: Mercator Medsystems, Inc., San Leandro, CA (US)

(*) Notice: Subject to any disclaimer, the term of this patent is extended or adjusted under 35 U.S.C. 154(b) by 235 days.

(21) Appl. No.: 10/447,676

(22) Filed: May 28, 2003

(65) Prior Publication Data

US 2003/0236494 A1 Dec. 25, 2003

Related U.S. Application Data

(60) Provisional application No. 60/384,894, filed on May 28, 2002.

(51) Int. Cl.  
*A61M 29/00* (2006.01)

(52) U.S. Cl. ............... 606/192; 606/194; 604/96.01; 604/99.01

(58) Field of Classification Search .......... 606/108, 606/192–195; 623/1.11; 604/96.01, 103.01, 604/103.09, 118–122, 97.01, 99.01–99.04  
See application file for complete search history.

(56) References Cited

U.S. PATENT DOCUMENTS

| | | |
|---|---|---|
| 4,016,863 A | 4/1977 | Brantigan |
| 4,638,805 A | 1/1987 | Powell |
| 4,692,200 A | 9/1987 | Powell |
| 4,715,378 A | 12/1987 | Pope, Jr. et al. |
| 4,810,455 A | 3/1989 | Pope, Jr. et al. |
| 4,821,722 A | 4/1989 | Miller et al. |
| 5,035,705 A | 7/1991 | Burns |
| 5,049,130 A | 9/1991 | Powell |
| 5,100,385 A | 3/1992 | Bromander |
| 5,176,698 A | 1/1993 | Burns et al. |
| 5,256,143 A | 10/1993 | Miller et al. |

*Primary Examiner*—(Jackie) Tan-Uyen Ho  
(74) *Attorney, Agent, or Firm*—Townsend and Townsend and Crew LLP

(57) ABSTRACT

An aspiration baffle comprises an outer tube and an inner core wire. Microholes are provided in the outer tubular member to permit passage of gas but inhibit the passage of liquids. The aspiration baffle is used in a catheter having a balloon or other inflatable structure to assist in priming of the structure. After evacuating the inflatable structure by applying a vacuum, the aspiration baffle can collect and trap residual gas which remains during the priming of the inflatable structure.

32 Claims, 3 Drawing Sheets

METHODS AND APPARATUS FOR ASPIRATION AND PRIMING OF INFLATABLE STRUCTURES IN CATHETERS

CROSS-REFERENCES TO RELATED APPLICATIONS

This application claims the benefit of U.S. Provisional Application No. 60/384,894, filed on May 28, 2002, the full disclosure of which is incorporated herein by reference.

BACKGROUND OF THE INVENTION

1. Field of the Invention

The present invention relates generally to medical devices and methods. More particularly, the present invention relates to apparatus and methods for removing air from vascular and other medical catheters having chambers which are filled with liquid.

Balloon angioplasty, stent treatment, and numerous other intravascular procedures employ catheters which are introduced to the vasculature and advanced intravascularly to a target location, often in the coronary vasculature. Many such intravascular catheters have inflatable balloons and other structures intended to effect or assist in performing a therapeutic procedure, e.g. balloon angioplasty, stent placement, and/or drug delivery. Such expandable structures can take a variety of forms, including non-distensible balloons of the type typically used for performing angioplasty, elastomeric balloons of the type often used for vessel occlusion, and driving structures of the type used for advancing needles and manipulating other tools.

Because of the dangers of the release of air into the bloodstream, such expandable structures are typically inflated with a liquid, such as saline, in order to achieve inflation within the vasculature. In order to purge the inflatable structures prior to use, the catheters are typically primed with liquid immediately prior to use. A common method of priming relies on vacuum aspiration of air from the inflatable structure through a lumen in the catheter, typically the inflation lumen which is subsequently used to introduce the liquid inflation medium. Thus, a vacuum is typically applied through the inflation lumen to lower the air pressure within the inflatable structure to a fraction of atmospheric pressure, typically 15 mm Hg or below. A liquid inflation medium is then introduced into the inflatable structure while preventing the reintroduction of air and other gasses.

While this procedure significantly limits the presence of air and other gasses within the inflatable structure, it will be appreciated that there will usually be a small residual amount of gas within the inflatable structure since the vacuum drawn is not complete. In order to even further enhance the safety, it is desirable to reduce or eliminate such residual gas amount within the inflatable structure.

The most common method for eliminating such residual gas in the balloon or other inflatable structure is to provide a vent tube or hole from the interior of the inflatable structure to the atmosphere. In this way, as the balloon or other inflatable structure is primed with liquid inflation medium, the residual air or gas will migrate toward the vent and be released into the atmosphere. The release of liquid medium is reduced or eliminated by providing vent tubes or holes having small or capillary dimensions. Thus, the vent tubes or holes will allow gas to pass but will inhibit the passage of the liquid inflation medium at the priming pressures and subsequent therapeutic pressures used in the procedures.

While the use of vent tubes and holes has been generally successful, the need to provide a passage from the interior of the inflatable structure to the atmosphere can compromise the integrity and design of the inflatable structure. Thus, it would be desirable to provide alternative and improved structures for removing or sequestering residual gas inside an inflatable structure on a vascular or other catheter prior to use. In particular, it would be desirable if the apparatus and methods did not require significant alteration in the structure of the balloon or other inflatable structure on the catheter. Some of these objectives will be met by the invention described herein below.

2. Description of the Background Art

Vascular catheters having balloons with vent structures are described in U.S. Pat. Nos. 4,638,805; 4,692,200; 4,715,378; 4,810,455; 4,821,722; 5,035,705; 5,049,130; 5,100,385; 5,176,698; and 5,256,143.

BRIEF SUMMARY OF THE INVENTION

The present invention provides apparatus and methods for purging gas from inflatable structures on intravascular and other medical catheters while said structures are being primed with a liquid inflation medium. While the inflatable structures will typically be angioplasty balloons, stent delivery balloons, elastomeric isolation balloons, embolectomy balloons, occlusion balloons, and like, there may also be other inflatable structures intended for distinct purposes. In particular, the purging apparatus and methods of the present invention may find particular use with inflatable structures intended for driving needles, cutting blades, and other tools and implements intended for intravascular and other therapeutic procedures.

In a first aspect of the present invention, an aspiration baffle for purging gas from a liquid-filled chamber in a catheter comprises a tubular member having a distal end, a proximal end, and an interior volume extending between said ends. The tubular member will be sealed over its entire surface except for a plurality of "microholes." The microholes have dimensions selected to permit the passage of gas under the differential pressures expected during the priming process. Such selected dimensions, however, will also inhibit or prevent the flow of liquid inflation medium through the microholes under the both the priming pressures as well as the inflation pressures expected during use of the catheter and vasculature. In angioplasty procedures, such inflation pressures can be as high as 10 atmospheres, 20 atmospheres, or even higher in some circumstances. Particular dimensions for the microholes are set forth below.

The tubular member of the aspiration baffle, will be adapted to be disposed axially in the catheter so that the microholes are present in the interior of the chamber which is first purged of gas and later filled with liquid inflation medium. Thus, the microholes will initially allow residual gas present in the inflatable chamber after initial vacuum aspiration to pass into the interior of the tubular member as a priming liquid is introduced, typically at atmospheric pressure or higher. While the inflatable chamber is being primed with the liquid inflation medium, the residual gas will thus be able to pass into the interior of the tubular member which remains at or close to the vacuum which had been achieved during the initial vacuum step. Thus, the aspiration baffle acts as a low-pressure reservoir or "sponge" for drawing and trapping the residual gas volume present in the inflatable chamber after the initial vacuum aspiration. The near-vacuum pressure is maintained since the gas volume is very low and the entrance of liquid into the interior of the tubular member (which liquid would quickly relieve the vacuum) is prevented by the small size of the microhole.

In a preferred construction, the aspiration baffle further comprises a core wire or other interior structure to provide mechanical strength. For example, the core wire may be coaxially disposed within the interior volume of the tubular member, running axially over at least a portion of the length of the tubular member, usually over the entire length. The exterior surface of the core wire and interior surface of the tubular member thus define an annular flow path or volume for receiving the residual gas through the microholes.

Typically, the tubular member will have a length in the range 12 cm to 200 cm, often from 20 cm to 150 cm. The tubular member will have an outside diameter usually in the range from 0.1 mm to 1 mm, and the microholes will have a maximum width, usually a diameter in the case of circular microholes, in the range of 0.001 mm to 0.1 mm. The microholes may extend over the entire length of the exterior of the tubular member, or may optionally extend over only a portion of the length, e.g. in the range from 1 cm to 20 cm. The microholes may be arranged axially in one or more rows, may be arranged spirally, or may be arrange in any other random or regular pattern. The number of microholes may range from 2 to 1,000, typically being from 5 to 500. The core wire may extend the entire length of the tubular member or, alternatively, may only extend through a portion thereof, typically from 1 cm to 100 cm.

In a second aspect of the present invention, a catheter comprises a catheter body having a proximal end, a distal end, and an inflation lumen therethrough. An inflatable chamber is disposed on the catheter body to receive inflation medium from the inflation lumen, and an aspiration baffle is disposed in the catheter body. The aspiration baffle defines a sealed interior volume open to an interior of the inflatable chamber through a plurality of microholes. Thus, by applying a vacuum to the interior of the inflatable chamber, typically through the inflation lumen, the interior volume of the aspiration baffle is initially evacuated to a sub atmospheric pressure. After such initial evacuation, the inflatable chamber is primed with a liquid inflation medium, typically at atmospheric pressure or higher, such that residual gas remaining after the initial evacuation passes from the inflatable chamber into the interior volume of the aspiration tube.

Depending on the desired use, the inflatable chamber may be an angioplasty balloon, may be adapted to carry an expandable tubular prosthesis, such as a stent, graft, or the like, or may carry a needle in order to effect extraluminal drug delivery. Optionally, the catheter body may also include a guide wire lumen. The aspiration lumen may optionally be held within yet another lumen within the catheter body. In some embodiments, the additional catheter body lumen may actually form part of the aspiration baffle, e.g. an end of the tubular member may be opened into a volume defined by the additional lumen in the catheter body. So long as said additional lumen were otherwise sealed, the luminal volume would then form part of the interior volume of the aspiration baffle. Other aspects of the aspiration baffle forming part of the catheter of the present invention have been described above with respect to the aspiration baffle embodiments.

In a third aspect of the present invention, a method for priming an inflatable chamber on a catheter with liquid comprises drawing a vacuum in the chamber through an inflation lumen in the catheter to remove gas from the chamber. Depending on the level of vacuum which is drawn, a residual amount of gas will be left in the inflatable chamber. The chamber is then filled or "primed" with a liquid, typically the same liquid which will be used for inflating the chamber during use. An aspiration baffle is disposed in the catheter body such that microholes are in communication with the interior of the inflatable chamber. The aspiration baffle is able to draw and sequester at least a major portion of the residual air or gas volume which remains in the inflatable chamber after the initial vacuum aspiration step. Typically, the initial vacuum will be drawn down to a pressure of about 15 mm Hg or lower, and the inflatable chamber will then be filled with liquid at a pressure of at least one atmosphere, and often two atmospheres or greater. Particular aspects of the aspiration baffle used in these methods are generally as described above in connection with the aspiration baffle itself.

DETAILED DESCRIPTION OF THE INVENTION

Figure 1:
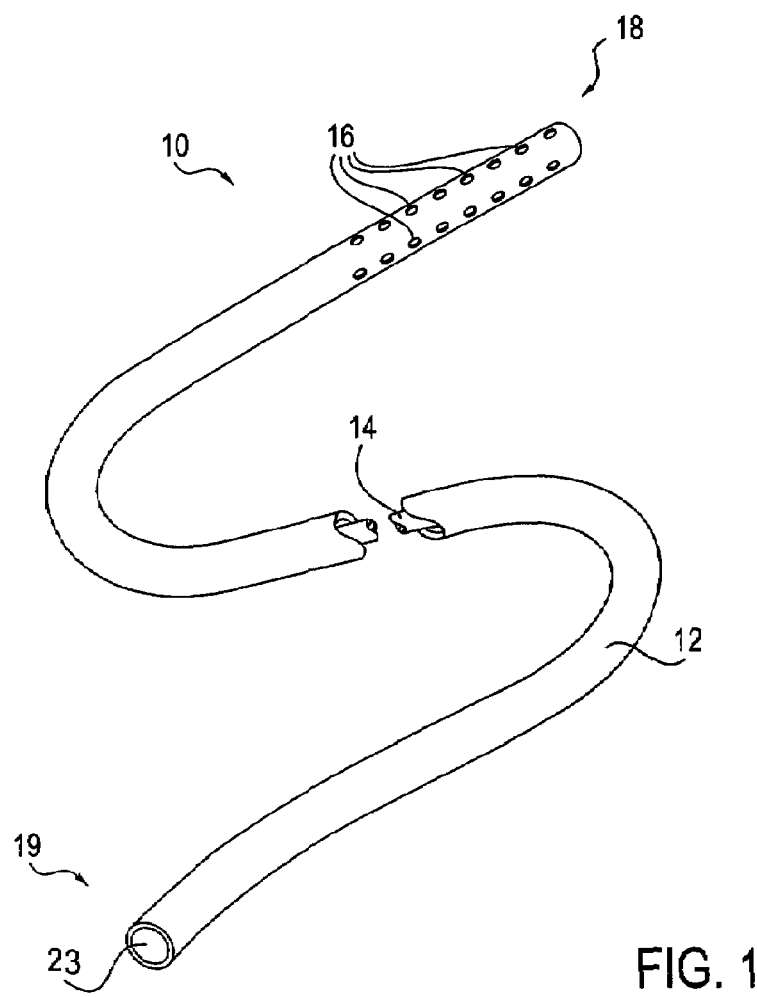
FIG. 1 is a perspective view of an aspiration baffle constructed in accordance with the principles of the present invention.
Figure 2:
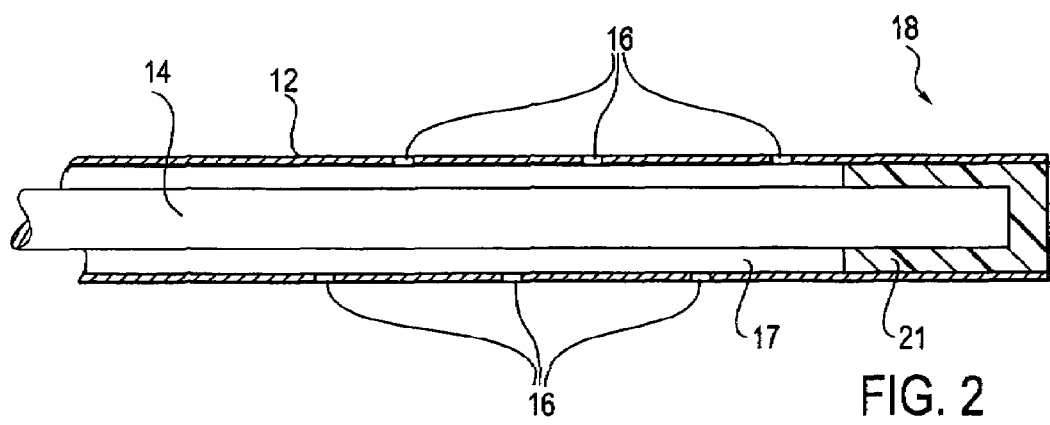
FIG. 2 is an enlarged distal end view of the aspiration baffle of FIG. 1, shown in partial section.

An aspiration baffle 10 constructed in accordance with the principles of the present invention comprises an outer tubular member 12 and, optionally, an inner core wire 14 (FIGS. 1 and 2). A plurality of microholes 16 are formed in the wall of the outer tubular member 12, thus defining passages from a region exterior to the aspiration baffle to an annular region 17 defined between an exterior surface of the core wire 14 and an interior surface of the outer tubular member 12 (FIG. 2). Core wire 14 is attached to the outer tubular member, for example by a polymeric plug 21 formed in a distal end 18 of the tubular member. A similar or alternative plug 23 is also provided at the proximal end 19 of the tubular member 12. Thus, the outer tubular member defines a completely sealed environment in its interior which is open to the exterior only through the microholes 16.

Note that while the tubular member 12 is shown in FIGS. 1 and 2 as being an integrated or self-contained unit, it is possible to form portions of the aspiration tube from other portions of the catheter into which it is to be placed. For example, the proximal end 20 may be left opened and attached to an interior lumen, receptacle, or other cavity or volume formed within the catheter body itself. In the latter case, however, it is still necessary that the cavity or volume provided in the catheter body be sealed so that the only passages between the interior of the aspiration baffle and the exterior (which is within the inflatable chamber on the catheters described herein below) be the microholes.

Figure 3:
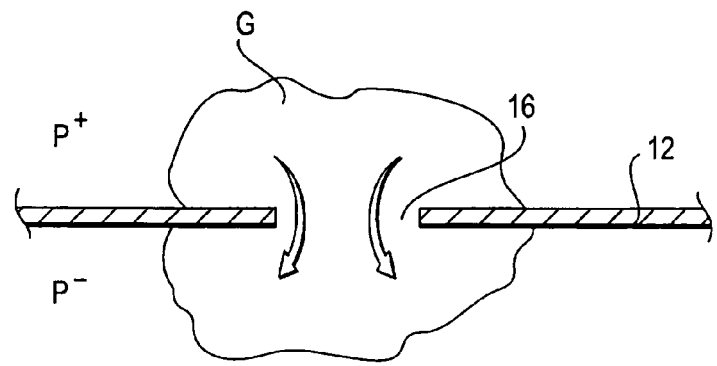
FIGS. 3 and 4 are schematic illustrations showing the difference in gas flow and liquid flow through a microhole of the dimensions utilized in the aspiration baffles of the present invention.
Figure 4:
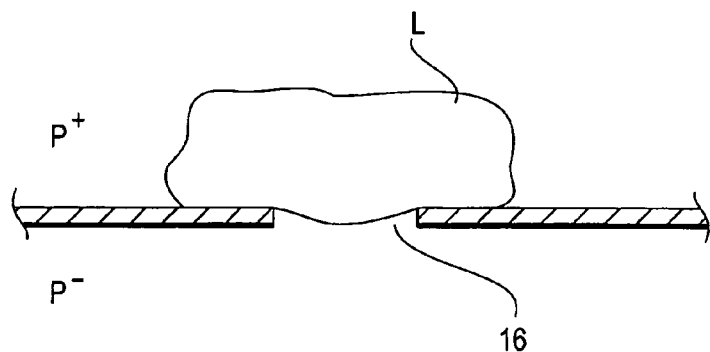

Referring now to FIGS. 3 and 4 the microholes 16 will have dimensions, generally as set forth above, which permit the flow of a gas G (FIG. 3) from a high pressure region ($P^+$) on one side of the tubular member 12 to a low pressure region (P⁻) on the other side of the member. Thus, the gas will flow in the direction of the arrows shown in FIG. 3. In the case of a liquid L, however, the dimensions of microholes 16 are selected so that flow is inhibited at the differential pressure between regions P⁺ and P⁻, as shown in FIG. 4.

Figure 5:
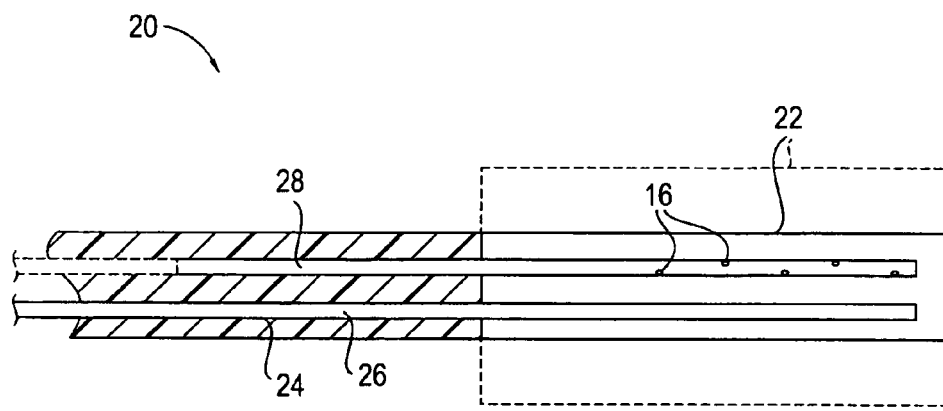
FIG. 5 is a schematic illustration of a balloon catheter comprising an aspiration baffle in accordance with the principles of the present invention.

Referring now to FIG. 5, a catheter 20 having an inflatable chamber in the form of a balloon 22 is schematically illustrated. The catheter 20 has an inflation lumen 24, it is shown with an optional inflation tube 26 which extends into the interior of the balloon 22. An aspiration baffle 28, which may be identical to baffle 10 illustrated above, it is disposed within the body of catheter 20 so that the microholes 16 on the baffle 28 are disposed within the interior of the balloon 22. The baffle 28 may extend proximally within the catheter by selected distance, optionally the entire distance of the catheter body. Optionally, as discussed above, portions of the interior volume of the aspiration baffle 28 may be formed by lumens or other internal cavities of the body of catheter 20.

The catheter 20 may be prepared for use in a patient as follows. A conventional balloon catheter vacuum and inflation device, such as those available from Guidant Corporation, Johnson & Johnson, Boston Scientific, and the like, is used to first draw a vacuum through the inflation lumen or tube 24/26 to a desired low pressure, typically about 15 mm of Hg. After the pressure has been achieved, the balloon 22 is then primed with saline or other inflation medium to a conventional pressure, typically one atmosphere, two atmospheres, or higher.

In the initial vacuum aspiration step, air or other gas from the interior of the aspiration baffle 28 is withdrawn through the microhole 16 together with the other air or gasses which are present in the balloon 22. When the liquid inflation medium is introduced into the balloon 22, however, the liquid is prevented from entering the interior of aspiration baffle 28 as the flow through individual microholes 16 is blocked, generally shown in FIG. 4 above. Thus, even though the pressure within the balloon quickly rises from vacuum to one atmosphere, two atmospheres, or higher, the pressure within the aspiration baffle remains at the near-vacuum level achieved during the initial vacuum aspiration step. The presence of the vacuum allows the residual gas remaining in the balloon 22 to migrate toward the microholes. When the gas reaches individual microholes, the gas will pass into the interior of the aspiration baffle, generally shown in FIG. 3 above, where it will remain since the interior pressure of the baffle remains significantly sub-atmospheric. Thus, during the priming step, at least a major portion of the residual air or other gas within the balloon will be collected and trapped within the interior of the aspiration baffle. Moreover, so long as the interior of balloon 22 contains the priming medium or subsequent inflation medium, the vacuum within the aspiration baffle will remain since liquid inflow is inhibited and the gas is retained because of the differential pressure, i.e. a vacuum within the interior of the baffle, an atmospheric or higher pressure within the interior of the balloon 22. Even if the balloon 22 should burst during use, the escape of gas through microhole 16 is still prevented since the blood which could enter the burst balloon would still maintain the seal on the microholes, thus preventing loss of hair or other gas.

Figure 6:
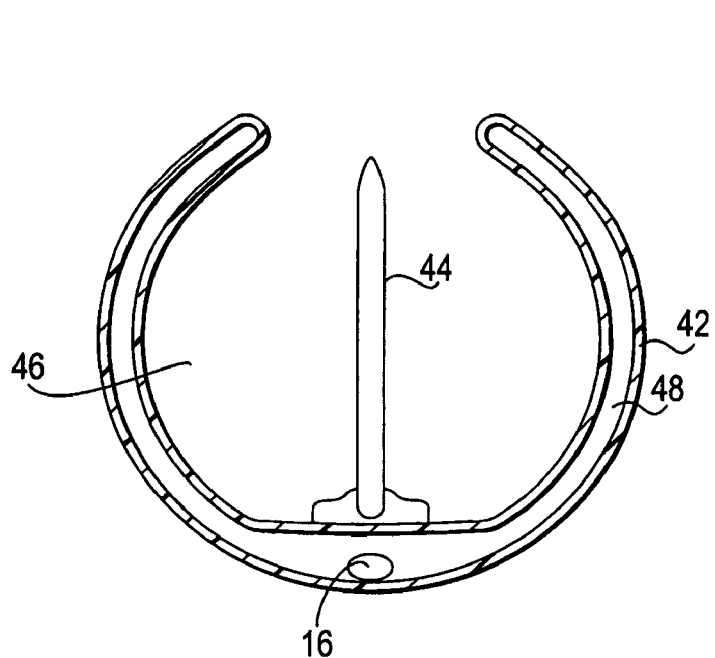
FIGS. 6 and 7 are a cross-sectional and end views of a needle injection catheter including an aspiration baffle in accordance with the principles of the present invention.
Figure 7:
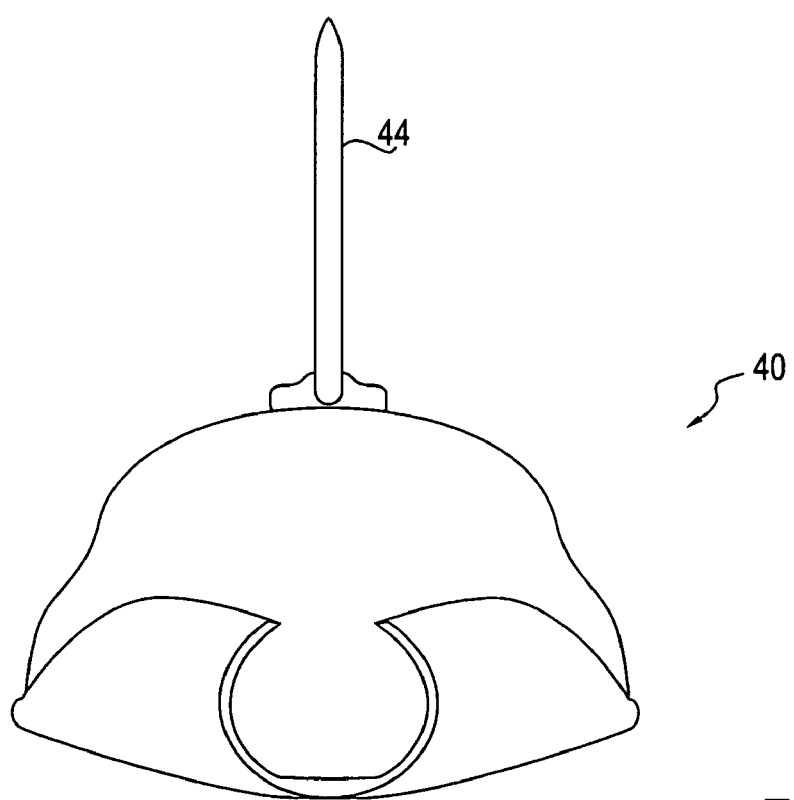

Catheter 20 of FIG. 5 is representative of a variety of balloon-type catheters, including angioplasty catheters, stent delivery catheters, balloon isolation catheters, balloon occlusion catheters, and the like. The aspiration tubes of the present invention, however, may find use with any type of catheter having an inflatable chamber which is to be inflated with a liquid inflation medium. For example, the aspiration baffles will find particular use with needle injection catheters such as those described in co-pending U.S. application Ser. Nos. 10/421,997 and 10/393,700, the full disclosures of which are incorporated herein by reference. An exemplary needle catheter employing the aspiration baffle of the present invention is illustrated in FIGS. 6 and 7. A catheter 40 comprises a structure 42 carrying a needle 44 within an involuted cavity 46 preformed within the catheter. The involuted structure is formed from the catheter body itself and includes a C-shaped inflatable interior 48 which receives an inflation medium from an inflation lumen (not shown). According to the present invention, the aspiration tube 16 may be provided through the catheter body and extending into the inflatable interior 48, as shown in FIG. 6. Thus, prior to inflation of the device, as shown in FIG. 7, the aspiration baffle 16 may be used to remove residual gasses during a priming procedure which may be performed identically to that described in connection with FIG. 5 above.

What is claimed is:

1. An aspiration baffle for purging gas from a liquid-filled chamber in a catheter, said baffle tube comprising:
   a tubular member having a distal end, a proximal end, and an interior volume extending between said ends, wherein the tubular member is sealed except for a plurality of microholes;
   wherein the microholes remain open when a vacuum is applied to the interior volume;
   said tubular member adapted to be disposed axially in the catheter so that the microholes are present in the liquid filled chamber to permit passage of gas from said chamber into the interior while substantially preventing the passage of liquid from said chamber into the interior.

2. An aspiration baffle as in claim 1, further comprising a core wire disposed coaxially within the interior volume of the tubular member, wherein an annular gas flow path is formed between an interior wall of the tubular member and an exterior surface of the core wire.

3. An aspirator baffle as in claim 2, wherein the tubular member has a length in the range from 2 cm to 200 cm and an outer diameter in the range from 0.1 mm to 1 mm, and wherein the microholes have a maximum width in the range from 0.001 mm to 0.1 mm.

4. An aspirator baffle as in claim 3, wherein the microholes are disposed over only a distal length of the tubular member in the range from 1 cm to 20 cm.

5. An aspirator baffle as in claim 4, wherein the core wire extends from the distal end of the tubular member over a distance in the range from 1 cm to 100 cm.

6. A catheter comprising:
   a catheter body having a proximal end, a distal end, and an inflation lumen;
   an inflatable chamber on the catheter body disposed to receive an inflation medium from the inflation lumen; and
   an aspiration baffle disposed in the catheter body, said baffle defining a sealed interior volume open to an interior of the inflatable chamber through a plurality of microholes only;
   wherein the interior volume of the aspiration baffle is evacuated through the microholes when a vacuum is applied to the interior of the inflatable chamber through the inflation lumen so that residual gas may pass from the inflatable chamber into the interior volume of said aspiration baffle tube when the inflatable chamber is subsequently filled with liquid.

7. A catheter as in claim 6, wherein the inflatable chamber is an angioplasty balloon.

8. A catheter as in claim 6, wherein the inflatable chamber carries an expandable tubular prosthesis.

9. A catheter as in claim 6, wherein the inflatable chamber carries a needle.

10. A catheter as in claim 6, wherein the catheter body also has a guidewire lumen.

11. A catheter as in claim 6, wherein the catheter body also has a lumen which receives the aspiration baffle.

12. A catheter as in claim 11, wherein the lumen which receives the aspiration baffle defines at least a portion of the sealed interior volume of the aspiration baffle.

13. A catheter as in claim 6, further comprising a core wire disposed coaxially within the interior volume of the tubular member, wherein an annular gas flow path is formed between an interior wall of the tubular member and an exterior surface of the core wire.

14. A catheter as in claim 13, wherein the tubular member has a length in the range from 10 cm to 200 cm and an outer diameter in the range from 0.1 mm to 1 mm, and wherein the microholes have a maximum width in the range from 0.001 mm to 0.1 mm.

15. A catheter as in claim 14, wherein the microholes are disposed over only a distal length of the tubular member in the range from 1 cm to 20 cm.

16. A catheter as in claim 15, wherein the core wire extends from the distal end of the tubular member over a distance in the range from 1 cm to 100 cm.

17. A catheter comprising:
a catheter body having a proximal end, a distal end, and an inflation lumen;
an inflatable chamber on the catheter body disposed to receive an inflation medium from the inflation lumen;
an aspiration baffle disposed in the catheter body, said baffle defining a sealed interior volume open to an interior of the inflatable chamber through a plurality of microholes only;
a needle carried by the inflatable chamber; and
wherein the interior volume of the aspiration baffle is evacuated through the microholes when a vacuum is applied to the interior of the inflatable chamber through the inflation lumen so that residual gas may pass from the inflatable chamber into the interior volume of said aspiration tube when the inflatable chamber is subsequently filled with liquid.

18. A catheter as in claim 17, wherein the catheter body also has a guidewire lumen.

19. A catheter as in claim 17, wherein the catheter body also has a lumen which receives the aspiration baffle.

20. A catheter as in claim 19, wherein the lumen which receives the aspiration baffle defines at least a portion of the sealed interior volume of the aspiration baffle.

21. A catheter as in claim 17, further comprising a core wire disposed coaxially within the interior volume of the tubular member, wherein an annular gas flow path is formed between an interior wall of the tubular member and an exterior surface of the core wire.

22. A catheter as in claim 21, wherein the tubular member has a length in the range from 10 cm to 200 cm and an outer diameter in the range from 0.1 mm to 1 mm, and wherein the microholes have a maximum width in the range from 0.001 mm to 0.1 mm.

23. A catheter as in claim 22, wherein the microholes are disposed over only a distal length of the tubular member in the range from 1 cm to 20 cm.

24. A catheter as in claim 23, wherein the core wire extends from the distal end of the tubular member over a distance in the range from 1 cm to 100 cm.

25. A catheter comprising:
a catheter body having a proximal end, a distal end, and an inflation lumen;
an inflatable chamber on the catheter body disposed to receive an inflation medium from the inflation lumen;
an aspiration baffle disposed in the catheter body, said baffle defining a sealed interior volume open to an interior of the inflatable chamber through a plurality of circular microholes only;
an expandable tubular prosthesis carried by the inflatable chamber; and
wherein the interior volume of the aspiration baffle is evacuated through the microholes when a vacuum is applied to the interior of the inflatable chamber through the inflation lumen so that residual gas may pass from the inflatable chamber into the interior volume of said aspiration baffle when the inflatable chamber is subsequently filled with liquid.

26. A catheter as in claim 25, wherein the catheter body also has a guidewire lumen.

27. A catheter as in claim 25, wherein the catheter body also has a lumen which receives the aspiration baffle.

28. A catheter as in claim 27, wherein the lumen which receives the aspiration baffle defines at least a portion of the sealed interior volume of the aspiration baffle.

29. A catheter as in claim 25, further comprising a core wire disposed coaxially within the interior volume of the tubular member, wherein an annular gas flow path is formed between an interior wall of the tubular member and an exterior surface of the core wire.

30. A catheter as in claim 29, wherein the tubular member has a length in the range from 10 cm to 200 cm and an outer diameter in the range from 0.1 mm to 1 mm, and wherein the microholes have a maximum width in the range from 0.001 mm to 0.1 mm.

31. A catheter as in claim 30, wherein the microholes are disposed over only a distal length of the tubular member in the range from 1 cm to 20 cm.

32. A catheter as in claim 30, wherein the core wire extends from the distal end of the tubular member over a distance in the range from 1 cm to 100 cm.

* * * * *